(12) United States Patent
Foser et al.

(10) Patent No.: US 10,058,405 B2
(45) Date of Patent: Aug. 28, 2018

(54) DENTAL RESTORATION MODEL

(71) Applicant: Ivoclar Vivadent AG, Schaan (LI)

(72) Inventors: Hans-Peter Foser, Balzers (LI); Oliver Voigt, Trübbach (CH)

(73) Assignee: Ivoclar Vivadent AG, Schaan (LI)

(*) Notice: Subject to any disclaimer, the term of this patent is extended or adjusted under 35 U.S.C. 154(b) by 0 days.

(21) Appl. No.: 15/115,476

(22) PCT Filed: May 22, 2015

(86) PCT No.: PCT/EP2015/061410
§ 371 (c)(1),
(2) Date: Jul. 29, 2016

(87) PCT Pub. No.: WO2015/185379
PCT Pub. Date: Dec. 10, 2015

(65) Prior Publication Data
US 2017/0007380 A1 Jan. 12, 2017

(30) Foreign Application Priority Data

Jun. 5, 2014 (EP) .................................. 14171268
Jun. 6, 2014 (EP) .................................. 14171444

(51) Int. Cl.
| A61C 13/34 | (2006.01) |
| A61C 13/08 | (2006.01) |
| A61C 13/00 | (2006.01) |
| B22C 7/02 | (2006.01) |
| B22C 9/08 | (2006.01) |

(Continued)

(52) U.S. Cl.
CPC ........ *A61C 13/081* (2013.01); *A61C 13/0003* (2013.01); *A61C 13/0028* (2013.01); *A61C 13/34* (2013.01); *B22C 7/02* (2013.01); *B22C 7/026* (2013.01); *B22C 9/08* (2013.01); *B29C 33/0061* (2013.01); *B29C 33/20* (2013.01); *B29K 2091/00* (2013.01); *B29K 2891/00* (2013.01); *B29L 2031/757* (2013.01)

(58) Field of Classification Search
CPC ............ A61C 13/0003; A61C 13/0028; A61C 13/081; A61C 13/34; B22C 7/02; B22C 7/026; B29C 33/0061
See application file for complete search history.

(56) References Cited

U.S. PATENT DOCUMENTS

| 4,081,019 A | 3/1978 | Kulig |
| 4,161,208 A | 7/1979 | Cooper |

(Continued)

FOREIGN PATENT DOCUMENTS

| CN | 2238026 Y | 10/1996 |
| CN | 103286262 A | 9/2013 |
| JP | 20110167726 A | 9/2011 |

*Primary Examiner* — James P Mackey
(74) *Attorney, Agent, or Firm* — Ann M. Knab; Thad McMurray

(57) ABSTRACT

A dental restoration model including a positive model (15) of a dental restoration piece. The positive model (15) defines at least the outer contour (36) of a dental restoration piece to be made using lost wax technology and is provided with a locating pin region which is defined especially according to a given optimization process. The locating pin region is provided with a guiding element (30) which accommodates and/or guides a material feeder (22, 24, 26 and 28).

13 Claims, 3 Drawing Sheets

(51) Int. Cl.
  *B29C 33/00* (2006.01)
  *B29C 33/20* (2006.01)
  *B29K 91/00* (2006.01)
  *B29L 31/00* (2006.01)

(56) References Cited

U.S. PATENT DOCUMENTS

| | | | |
|---|---|---|---|
| 7,946,334 B2* | 5/2011 | Marshall | B22C 7/02 |
| | | | 164/235 |
| 2008/0142183 A1 | 6/2008 | Marshall et al. | |
| 2016/0089220 A1* | 3/2016 | Ebert | A61C 13/0004 |
| | | | 700/98 |

* cited by examiner

DENTAL RESTORATION MODEL

CROSS-REFERENCE TO RELATED APPLICATIONS

This application is a National Stage application of International patent application PCT/EP2015/061410 filed on May 22, 2015, which claims priority to European patent application No. 14171444.4 filed on Jun. 6, 2014 and European patent application No. 14171268.7 filed on Jun. 5, 2014, all the disclosures of which are incorporated herein by reference in their entirety.

FIELD OF THE INVENTION

The invention relates to a dental restoration model having a positive model of a dental restoration piece.

BACKGROUND OF THE INVENTION

It has been known for long to produce dental restorations by means of positive models which are cast with gypsum. After curing, the positive model is removed, usually by melting out. In traditional technology, it consists of wax such that the term "lost wax technology" has become established for the entire process.

In order to be able to produce several dental restoration models in one go several positive models are also required which are connected to one another via so-called sprue channels or material feeders. With the finished negative mold, the cavities for the dental restorations can be filled together and in one go.

Basically, processes of this type are also usual for the casting of dental restoration parts. In the pressing technology, it needs to be taken into account additionally that the produced muffle of gypsum is sufficiently strong to prevent so-called muffle cracks which, as a rule, result in a loss of the entire dental restoration which has been produced. Here, the wall thickness between the outer edge of the muffle and the closest adjacent position of the positive model or the related mold cavity is particularly relevant. Said wall thickness should not fall below a certain degree, for instance three centimeters.

On the other hand, it is desired to produce as many dental restorations as possible simultaneously such that particular effort is made to distribute the dental restoration in the manner of a wax tree by means of a corresponding number and arrangement of material feeders or sprue channels, based on a so-called muffle mandrel whose shape corresponds to the resulting press channel.

By now, it has also been known for a long time to produce the positive model by rapid prototyping and to use the model produced in this way as a basis for the molding process. An example of a solution of this type may be taken from WO/95/28688.

Also, it has already been suggested to optimize the exact position of the material feeder, its angle relative to the positive model and the so-called sprue region, that is to say the region at which material feeder and positive model meet, by software. In this connection, a good solution may be taken from the European patent application 14 171 268.7. Typically, the so-called sprueing process takes place obliquely from the side in the region of the occlusal or rather incisal side of the dental restoration.

However, it has also been known for a longer time to use green products with color gradients and to impart a corresponding color gradient to the tooth which is to be produced.

An example of this is the solution known from EP 2 065 012 A1, which already represents an improvement of the original so-called multi press process which has also been developed by the present applicant.

Besides the production by means of rapid prototyping it is also possible to produce the positive model with the related material feeder by milling by means of a CNC machine. Typically, this works for not too complex and contorted structures of the wax tree to be produced in this manner, as above a certain degree of complexity the milling cutter— even in case of five-axis milling machines—cannot reach the proper position to achieve the desired milling result.

Typically, green products of this type are produced from specific polymers which can be milled easily, but which can also be burnt out easily and which are milled from a solid block, in most cases from a disc having a diameter or 98.5 mm which is prepared for a standard milling reception.

Discs of this type can, for instance, have a thickness of 3 cm such that the integrated production of a wax tree having a corresponding height would also be possible if the above-mentioned problem did not exist.

Typically, the positive model is milled together with its related material feeder or sprue channel, readily in combination with one or several further positive models.

In this connection, comparatively much material is lost as the reproduction of the wax tree occupies a corresponding amount of space of the green product disk.

In the realization of mold cavities for dental restoration using the lost wax technology, another problem is that the muffles used for this purpose are surprisingly prone to muffle cracks. Typically, the lost material has a larger coefficient of thermal expansion than the surrounding gypsum material.

In case the heating does not take place exactly according to instruction, a plug of material can arise which initially obstructs the flow of wax to the outside and which leads to such a high positive pressure in the mold cavity due to the different coefficients of thermal expansion that the formation of cracks arises.

SUMMARY OF THE INVENTION

Contrary to this, the invention is based on the task of providing a dental restoration model according to the claims which is particularly suitable for the especially efficient and also fail-safe production using the lost wax technology.

This task is inventively solved by the independent claims. Advantageous developments may be taken from the sub-claims.

According to the invention, it is particularly favorable that by not producing the material feeder by means of rapid prototyping or by not milling it by means of a CNC machine the respective milling work or set-up work can be saved. When milling from a solid disc the dental restoration parts/ positive models can be moved closer to one another such that the available material can be utilized considerably better. This holds particularly true for the production of individual crowns which had to be provided with a material feeder each up to now whose volume could, for instance, amount to 30% of the crown. Typically, the material feeder also comprised a considerable length, such as, for instance, 50% or even 100% of the crown. This kept adjacent crowns at a distance correspondingly, particularly in the realization of entire wax trees in the green product disc.

According to the invention, it is now refrained from the combined production together with the material feeder or the sprue channel. Only one guiding element is provided which can be collar-shaped in particular. This guiding element can either protrude in the form of a bulge from the sprue region, or it can be incorporated in the positive model itself.

In both cases, an accommodation region for the material feeder is provided which can be produced from conventional wax as a standard element, and which is pressed into the accommodation region easily.

Typically, conventional wax melts already at 80° C., while the plastic material for the positive model which can be milled typically melts at about 120° C. Surprisingly, the formation of plugs in the region of the sprue channel—and thus the tendency towards muffle cracks when the muffle is not heated perfectly—can be reduced considerably due to a proper choice of materials in this connection.

In an advantageous embodiment, the material feeder is fabricated of a wax having a melting point of between 50° C. and 150° C.

In addition to the material savings of the polymer material for the provision of the positive models, which polymer material can be milled and is of high quality in most cases, the CNC machine saves time during the milling process. For the provision of the inventively configured material feeder wax devices known per se having a thickness of, for instance, 2.5 mm or 3 mm can easily be used which can be provided with an insertion chamfer manually by a brief pressing between two fingers in an advantageous embodiment. Typically, conventional wax can be deformed already at room temperature to a certain degree such that it is particularly suitable for the provision of the inventive material feeder.

It is also possible to use pre-fabricated material feeders which have preferably already been provided with an insertion chamfer in this case, for instance also made of conventional wax, which have already been ready-made and only need to be inserted into the accommodation region of the guiding element.

The insertion chamfer can be configured in any desired way as a cone on the material feeder—and on a corresponding and matching cone of the guiding element—, or can be provided at the material feeder in a convexely curved shape, then again preferably with a correspondingly concavely configured shape at the guiding element.

It is favorable if the inside of the guiding element and the associated outside of the material feeder match one another. This prevents gypsum particles from penetrating thereat.

If there is a free space between the internal cone and the external cone, it is favorable if the guiding element seals against the material feeder at its distal end in a ring-shaped manner.

In fact, it would basically be possible to bluntly press the material feeder to the sprue region of the positive model. However, according to the invention it is essential that an alignment between the axis of the material feeder and the positive model of the dental restoration takes place. For instance, the alignment can be carried out as is described in the European patent application 14 171 268.7 and corresponding US 20160089220, which is hereby incorporated by reference.

The inventive guiding element provides an alignment accuracy of +/−2° to 5° with a lean design, as is illustrated for instance in FIG. 2, or between 10° and 15° with a stump-type design, as is illustrated for instance in FIG. 3.

In this respect, the guiding element does not only determine the sprue region at the positive model predetermined by CAD, but at the same time the alignment of the material feeder relative to the positive model.

In an advantageous embodiment it is provided that the guiding element—optionally together with the positive model—is produced by rapid prototyping or CAD/CAM and that the outer contour of the guiding element (30) is determined in adaptation to the positive model and the inner contour (40) of the guiding element (30) as a standard, based on the predetermined shape of the material feeder (22 to 28).

In a further advantageous embodiment it is provided that the guiding element is at least partially accommodated in the positive model and that in particular the material feeder immerses into the positive model.

In a further advantageous embodiment it is provided that the guiding element is formed as a part of the positive model, in particular integrally with the positive model.

In a further advantageous embodiment it is provided that the guiding element is arranged on an occlusal or incisal side of a dental restoration and that it is round.

In a further advantageous embodiment it is provided that the guiding element is attached to a mesial or distal surface of a dental restoration and extends across a large part of the gingival/occlusal, or else the gingival/incisal height, in particular across approximately half of it, and that in particular the guiding element has a slot-shaped opening, and that the material feeder has a matching block-shaped construction.

In another advantageous embodiment, the material feeder is configured in a cylinder-shaped manner and that the guiding element surrounds the material feeder circularly or at least in a partially circle-shaped manner.

BRIEF DESCRIPTION OF THE DRAWINGS

Further advantages, details and features may be taken from the following description of several exemplary embodiments of the invention in conjunction with the drawings, in which.

DETAILED DESCRIPTION

Figure 1:
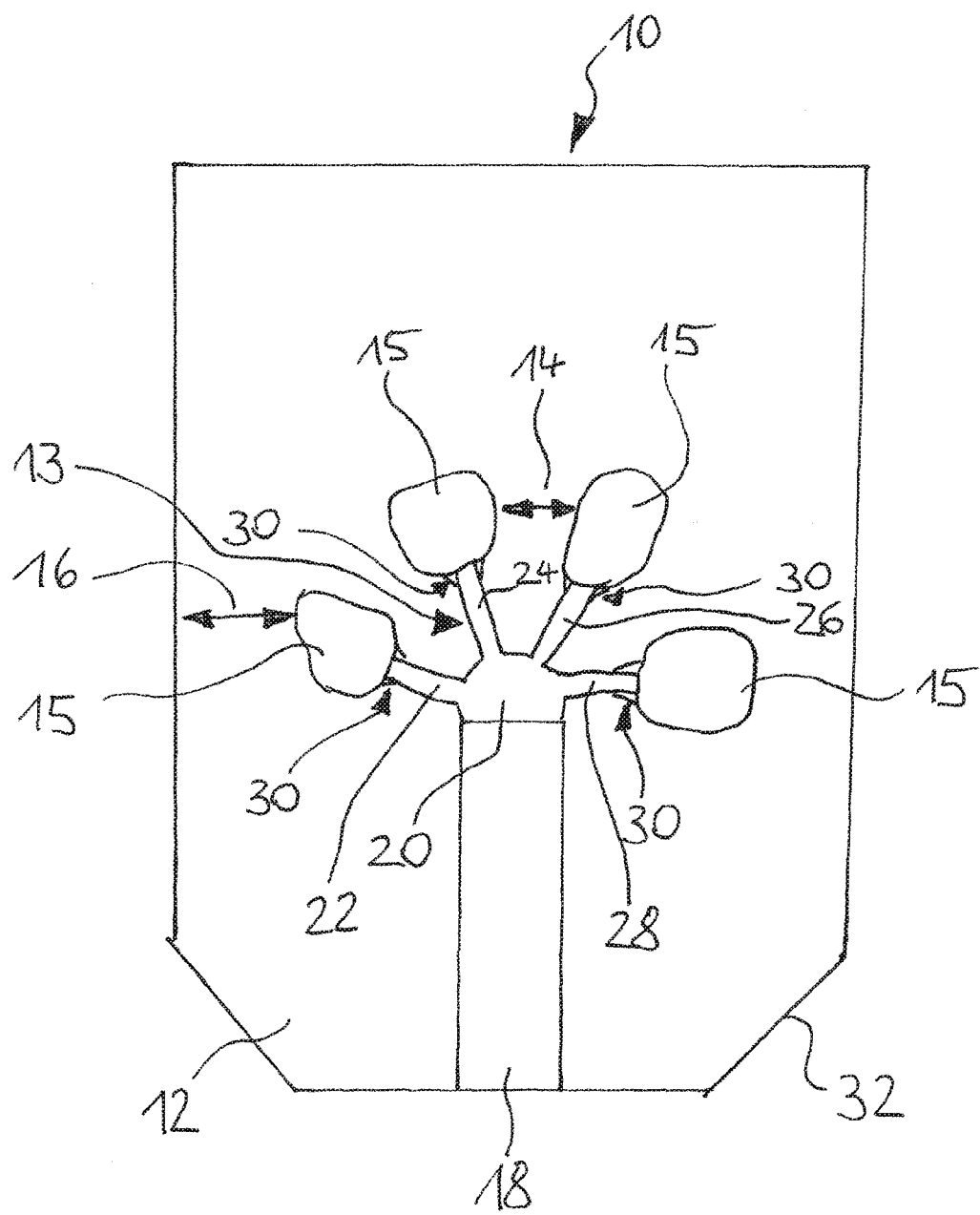
FIG. 1 shows a schematic illustration of an inventive dental restoration model in a multiple arrangement, that is to say with several positive models, in one embodiment.

In FIG. 1 a dental restoration model 10 is illustrated in a quadruple arrangement just like it is typically provided in a muffle 12. The four dental restoration models 10 illustrated in FIG. 1 are illustrated to be arranged in one plane for reasons of a simpler illustration, wherein it is to be understood that a so-called wax tree 13 which carries the dental restoration models 10 can be a three-dimensional tree in fact.

According to the arrangement a distance 14 between individual positive models cannot be undercut, and an edge distance 16 to the edge of the muffle 12 cannot be undercut either. For instance, the minimum distance 14 can be 2 cm and the minimum edge distance 16 can be 3 cm.

In a way known per se, the muffle 12 comprises a press channel 18. For the provision of the inventive dental restoration models 10 prior to casting the muffle 12 a so-called growth mandrel is typically inserted at the position at which the press channel 18 comes to rest later. On the tip of the growth mandrel a growth base 20 is attached, and material feeders 22, 24, 26 and 28 are attached to it appropriately. Both the growth base 20 and the material feeders 22 to 28 consist of conventional wax.

According to the invention, positive models 15, each comprising guiding elements 30, are fit onto the free ends of the material feeders 22 to 28. The design of guiding surfaces of the guiding elements 30 is selected such that both the position and the angle are determined exactly, in terms of the associated respective positive model 15.

In the exemplary embodiment illustrated, the positive models 15 are milled from solid blocks by CNC; however, in a modified embodiment they can also be produced by rapid prototyping. They consist of any desired suitable wax or plastic material which can be milled, such as a polymer, wherein the melting point thereof is preferably considerably higher than the melting point of the growth base 20 and the material feeders 22 to 28. Accordingly, the material feeder 22, 24, 26 and 28 has a lower melting point than the guiding element 30 and/or the positive model.

In this state, an appropriate sleeve is pulled over the growth mandrel with the dental restoration models 10 in a way known per se, and gypsum is cast to produce the muffle 12.

After it has cured, the growth mandrel is drawn out from the press channel 18 which has been formed now by means of a slight rotational movement. An initial heating to, for instance, 90° C. or 100° C. takes place. In this state, the muffle loses remaining residual moisture, and moreover the entire wax material in the regions of the material feeders 22 to 28, but also at the growth base 20, melts. It flows off completely via the press channel 18, wherein the muffle can be tilted slightly if necessary to enable residual material to flow out.

By the way, the tilting process is slightly simplified by the cone 32 which, by itself, serves to Facilitate the operation of a furnace hood in a press furnace.

When the conventional wax has completely flown out, the muffle 12 is heated further, in a way known per se by means of a ring heating, for instance. Now, the plastic material in the cavities also melts, said cavities corresponding to the positive models 15. The plastic material flows off, too, in turn optionally facilitated by a slight tilting of the muffle 12 in an appropriate manner.

For this reason, the combination of a material feeder which melts early and a positive model which melts late is particularly important as heating typically takes place from the outside such that the heat initially enters into the respectively located positive model 15 in the outer edge, after it has overcome the edge distance 16, and causes melting thereof in this position.

At this point in time, the material of the associated material feeder 22—unless is consists of Conventional wax—has not melted such that considerable pressure is produced by means of the thermal expansion which could make a muffle of an earlier invention burst; at the same time, the hard material feeder used to act like a plug.

According to the invention, this problem has now been solved.

Figure 2:
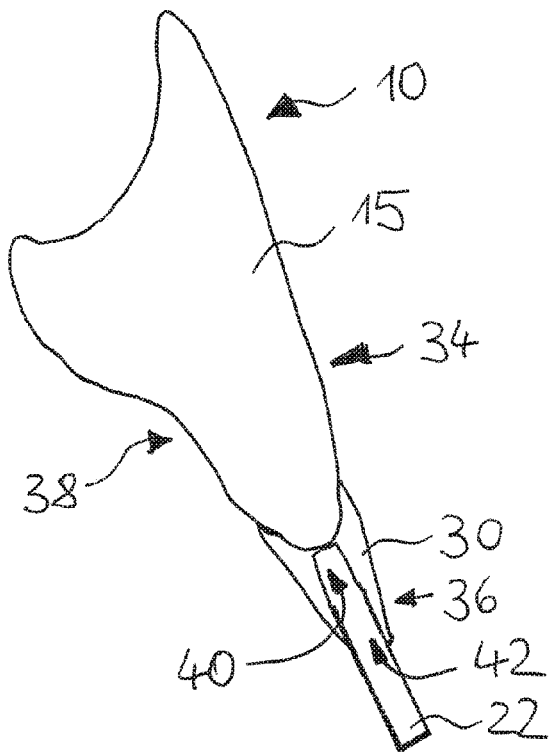
FIG. 2 shows a schematic illustration of an anterior tooth as a positive model, taking into account the inventive guiding element and the inventive material feeder, as viewed from the mesial direction.

FIG. 2 illustrates how a guiding element 30 can be configured. An anterior tooth is illustrated, and the guiding element 30 extends as an extension of the labial side 34 of the anterior tooth comprising a conical outer contour 36.

The same holds true for the lingual side 38 of the anterior tooth and the guiding element 30; here, too, the outer contour 36 extends as an extension of the lingual side.

In this way, no discontinuities occur, which could form ribs in gypsum which could tend to break during the pressing process.

The guiding element 30 also comprises an inner contour 40 which exactly matches the respective material feeder 22. The material feeder 22 is inserted into the accommodation region 42 of the guiding element 30 and bears flush at every position thereat. In the exemplary embodiment illustrated in FIG. 2, the material feeder 22 simply consists of a waxed rod having a diameter or 2.5 mm, that is to say without insertion chamfer, and is inserted into the guiding element 30 cautiously. The guiding element 30 is slightly harder than the material feeder 22 also at room temperature. The guiding element 30 abuts on the material feeder 22, 24, 26 and 28 on the outside and the outer contours 36 of the guiding element 30 and the material feeder 22 to 28 are able to merge together into one another continuously, without any places of discontinuity.

In any case, the material feeder 22 is inserted up to the stop at the positive model 15.

The outer contour 36 of the guiding element 30 is designed in a tooth-specific manner in order to achieve the desired continuous transition to the design of the positive model 15. However, the inner contour 40 is predetermined and stored in the CAD database in correspondence with the material feeders 22 used.

In this way, it is possible, for instance, to use a material feeder having a thickness of 2.5 mm or 3 mm depending on the size of the respective positive model 15 in order to adjust the flow of material or the respectively produced flow resistance to the requirements in the later pressing process.

Even if the invention is described with regard to a pressing process in this case, it is to be Understood that corresponding solutions are also possible analogously when realizing dental restoration parts by means of a casting technology.

Figure 3:
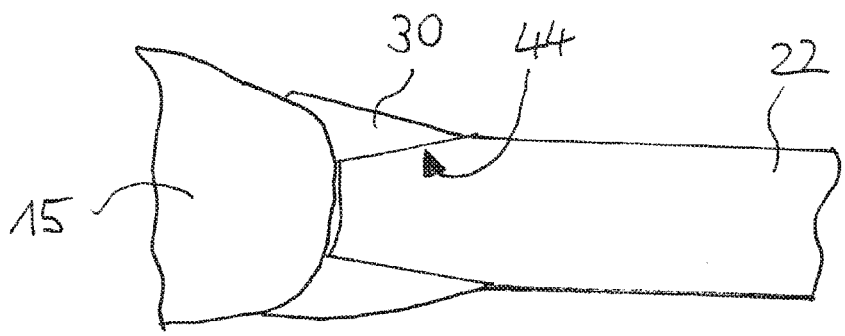
FIG. 3 shows a further embodiment of a part of an inventive dental restoration model, comprising a positive model, the guiding element and the material feeder.

FIG. 3 illustrates how the material feeder 22 and the guiding element 30 can be provided with an insertion chamfer 44 in a modified embodiment. In this embodiment, the guiding element 30 is comparatively short and accordingly requires and even lower input of material in the production. Preferably, the length of the guiding element, with regard to the length of the positive model, is between one twentieth and one third, particularly preferably between one twelfth and a fifth of the length of the positive model.

The guiding element (30) comprises an exposed accommodation area for the material feeder 22, 24, 26 and 28 which has a depth of which is at most 80% or less than, preferably less than 40% and particularly preferably about 20% of the length of the material feeder 22, 24, 26 and 28.

Figure 4:
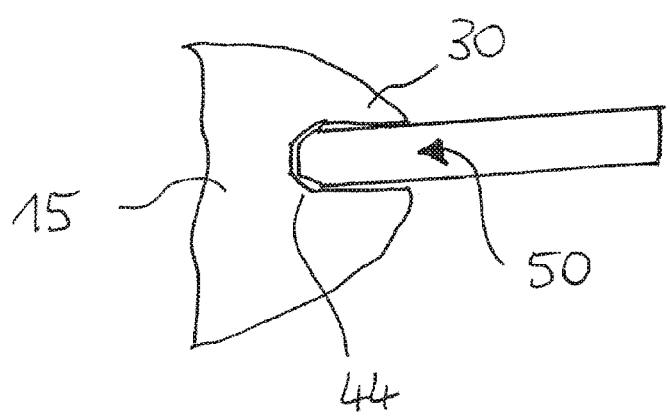
FIG. 4 shows a further embodiment of an inventive dental restoration model.

In the embodiment according to FIG. 4 it is provided to configure the guiding element 30 as an integral part of the positive model 15. Without further ado, a correspondingly shaped blind hole 50 is formed in the positive model 15. Here too, the realization of an insertion chamfer 44 is possible in order to facilitate the insertion.

Figure 5:
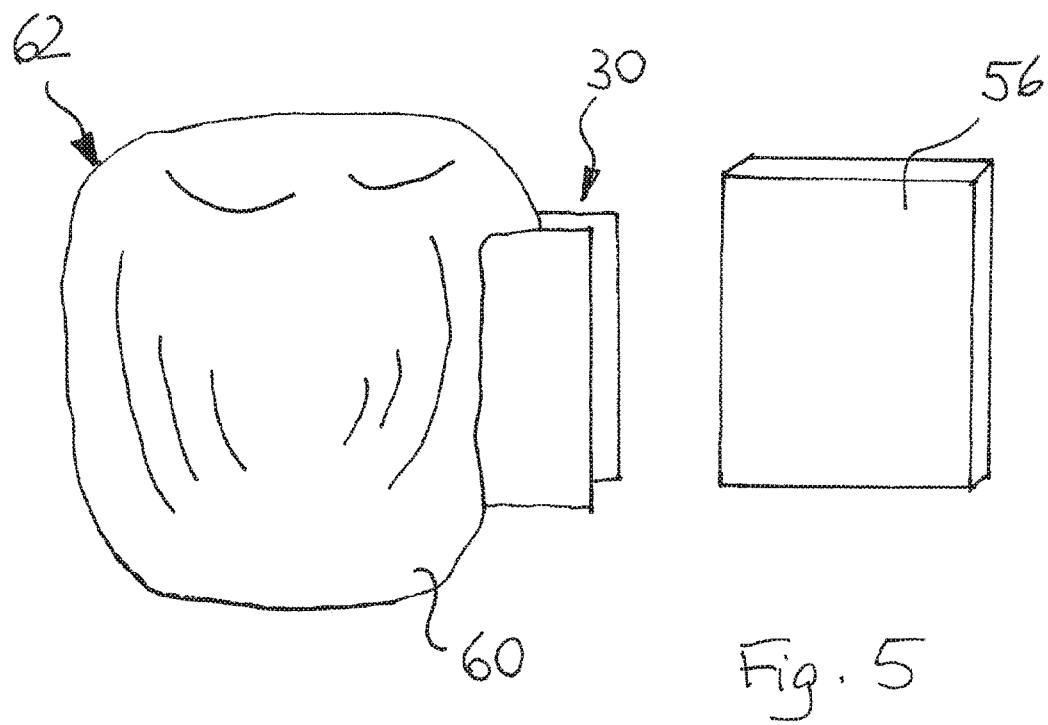
FIG. 5 shows a perspective side view of an inventive dental restoration model for the provision of the multi press process in a further embodiment of the invention.

FIG. 5 illustrates an inventive solution for the provision of a dental restoration model 10 by means of a multi press technology. Here, the guiding element 30 is formed by two plate stumps which extend slightly conically on the inside and which are intended to receive the material feeder 56 in between them in a clamping and/or snapping manner. In the multi press technology according to FIGS. 5 and 6 a color gradient is achieved, from darker color shades in the gingival region to more translucent color shades in the occlusal region 62 of the respective molar 60.

Figure 6:
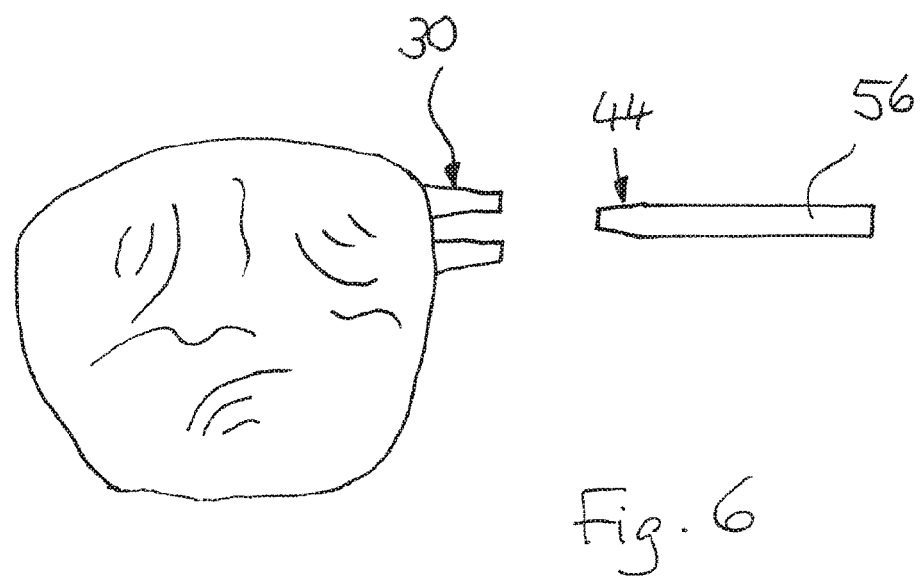
FIG. 6 shows the dental restoration model according to FIG. 5, however, as viewed from the occlusal view.

Here too, the arrangement of the guiding element 30 is determined by CAD such that the material supply by means of the material feeder 56 is aligned ideally with regard to the correct angle; here too, it is favorable that the material feeder 56 consists of conventional wax with a low melting point. The insertion chamfer 44 indicated in FIG. 6 is optional, however, it possibly facilitates the insertion, particularly with a heavily clamping design of the fit between the guiding element 30 and the material feeder 56.

In an alternative embodiment which is not illustrated a height stop is additionally provided which exactly determines the relative height in the gingival/occlusal direction of the material feeder 56 with regard to the guiding element 30.

The invention claimed is:

1. A dental restoration model comprising
a positive model (15) of a dental restoration piece, said positive model (15) defining at least an outer contour (36) of a dental restoration piece to be made using lost wax technology and being provided with a sprue region,
characterized in that the sprue region is provided with a guiding element (30) which accommodates and/or guides a material feeder (22, 24, 26 and 28), wherein the material feeder (22, 24, 26 and 28) has a lower melting point than the guiding element (30) and/or the positive model,
wherein the guiding element (30) comprises at least two fingers which extend away from the positive model (15) and form an accommodation area therebetween to receive the material feeder (22, 24, 26 and 28).

2. The dental restoration model as claimed in claim 1, characterized in that the guiding element (30) accommodates the material feeder (22, 24, 26 and 28) in a clamping and snapping manner.

3. The dental restoration model as claimed in claim 1, characterized in that the guiding element (30) abuts the material feeder (22, 24, 26 and 28) on an outside surface and in that an inner contour (36) of the guiding element (30) and an outer contour of the material feeder (22 to 28) merge together continuously, without any discontinuity.

4. The dental restoration model as claimed in claim 1, characterized in that the guiding element (30) comprises an outer contour (36) which merges into the outer contour (36) of the positive model (15) of the dental restoration continuously, without any discontinuity.

5. The dental restoration model as claimed in claim 1, characterized in that the guiding element (30) comprises an exposed accommodation area for the material feeder (22, 24, 26 and 28) having a depth of 80% or less than the length of the material feeder (22, 24, 26 and 28).

6. The dental restoration model as claimed in claim 1, characterized in that a part of the material feeder (22 to 28) can be inserted into the guiding element in a snapping and/or clamping manner.

7. The dental restoration model as claimed in claim 1, characterized in that the material feeder (22, 24, 26 and 28) comprises an insertion chamfer (44) by means of which the insertion chamfer (44) is insertable into an accommodation area of the guiding element (30).

8. The dental restoration model as claimed in claim 1, characterized in that the guiding element (30) adjacently abuts a distal end of the material feeder (22, 24, 26 and 28) in a sealing manner.

9. The dental restoration model as claimed in claim 1, characterized in that the material feeder (22, 24, 26 and 28) comprises a wax having a melting point of between 50° C. and 150° C.

10. The dental restoration model as claimed in claim 1, characterized in that the material feeder (22, 24, 26 and 28) and the guiding element (30) abut each other over an entire length of an insertion depth of the material feeder (22 to 28) into the guiding element (30).

11. The dental restoration model as claimed in claim 1, characterized in that the positive model (15) is connected with or abuts the material feeder (22, 24, 26 and 28) and that the material feeder (22, 24, 26 and 28) is made of a material having a lower melting point than a material of the positive model (15).

12. The dental restoration model as claimed in claim 5, characterized in that the depth of the exposed accommodation area of the guiding element (30) is less than 40% of the length of the material feeder (22, 24, 26 and 28).

13. The dental restoration model as claimed in claim 5, characterized in that the depth of the exposed accommodation area of the guiding element (30) is about 20% of the length of the material feeder (22, 24, 26 and 28).

* * * * *